(12) United States Patent
Jamison et al.

(10) Patent No.: US 11,143,540 B2
(45) Date of Patent: Oct. 12, 2021

(54) REAL TIME FLOW RATE METER

(71) Applicant: Halliburton Energy Services, Inc., Houston, TX (US)

(72) Inventors: Dale E. Jamison, Humble, TX (US); Xiangnan Ye, Cypress, TX (US)

(73) Assignee: Halliburton Energy Services, Inc., Houston, TX (US)

(*) Notice: Subject to any disclaimer, the term of this patent is extended or adjusted under 35 U.S.C. 154(b) by 162 days.

(21) Appl. No.: 16/666,203

(22) Filed: Oct. 28, 2019

(65) Prior Publication Data

US 2021/0123789 A1    Apr. 29, 2021

(51) Int. Cl.
*G01F 25/00* (2006.01)
*E21B 21/08* (2006.01)
*G01N 33/28* (2006.01)
*G01F 1/36* (2006.01)

(52) U.S. Cl.
CPC .......... *G01F 25/0007* (2013.01); *E21B 21/08* (2013.01); *G01F 1/36* (2013.01); *G01N 33/2823* (2013.01)

(58) Field of Classification Search
CPC ........ G01F 25/0007; G01F 1/36; E21B 21/08; G01N 33/2823
See application file for complete search history.

(56) References Cited

U.S. PATENT DOCUMENTS

| 5,135,684 | A | 8/1992 | Mohn et al. |
| 5,197,633 | A | 3/1993 | Hines et al. |
| 5,365,795 | A | 11/1994 | Brower |
| 6,681,189 | B1* | 1/2004 | Morrison ............... G01F 1/36 702/100 |
| 7,138,929 | B2 | 11/2006 | Jeffryes et al. |
| 8,065,923 | B2 | 11/2011 | Duhanyan et al. |
| 9,581,475 | B2 | 2/2017 | Johnson et al. |
| 2005/0284236 | A1* | 12/2005 | Kielb ................... G01F 1/42 73/861.42 |
| 2016/0076322 | A1* | 3/2016 | Oddie ............... G01F 25/0053 73/152.51 |
| 2017/0198536 | A1* | 7/2017 | Song ................ E21B 41/0092 |

(Continued)

FOREIGN PATENT DOCUMENTS

| BR | PI0716672 A2 | 9/2013 |
| KR | 20070018007 A | 2/2007 |

OTHER PUBLICATIONS

Thomas, David G., 1965, Transport Characteristics of Suspension: VIII. A Note on the Viscosity of Newtonian Suspensions of Uniform Spherical Particles, Journal of Colloid Science, 20, pp. 267-277.

(Continued)

*Primary Examiner* — Herbert K Roberts
*Assistant Examiner* — John M Royston
(74) *Attorney, Agent, or Firm* — McGuireWoods LLP

(57) ABSTRACT

A system and method for calibrating discharge coefficients using either an orifice plate flow rate meter or a venturi flow rate meter in a well operation is provided. Using differential pressures obtained from the flow rate meter along with real time calibration of the discharge coefficient with density and rheology data, the flow rate meter can be used in a much more analytical manner. In this way, real time detection of influx or cuttings can be determined in real time, along with estimated concentrations.

20 Claims, 5 Drawing Sheets

(56) References Cited

U.S. PATENT DOCUMENTS

2017/0306724 A1\* 10/2017 Forstner ................. E21B 21/08
2020/0003599 A1\* 1/2020 Theuveny ............... G01F 1/712

OTHER PUBLICATIONS

Butteur Mulumba Ntamba Ntamba; "Non-Newtonian Pressure Loss and Discharge Coefficients for Short Square-edged Orifice Plates"; Thesis for the degree Master Technology: Mechanical Engineering in the Faculty of Engineering, Nov. 2011; Cape Peninsula University of Technology.

Ni, Chunjian; "Numerical simulation of low Reynolds number pipe orifice flow"; Theses and Dissertations—Iowa State University; 2003.

\* cited by examiner

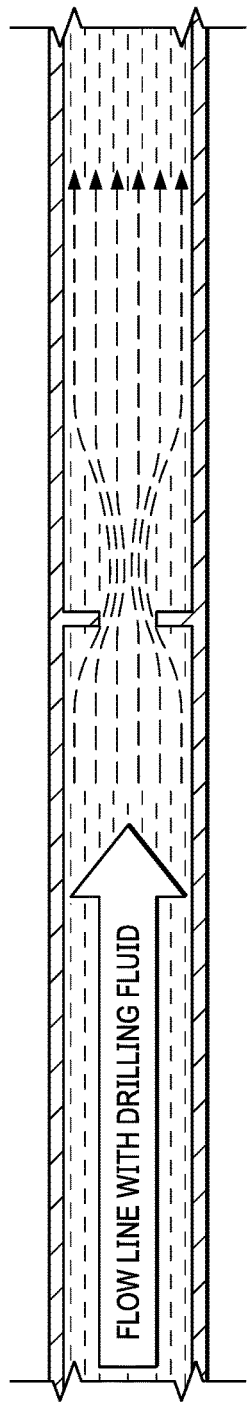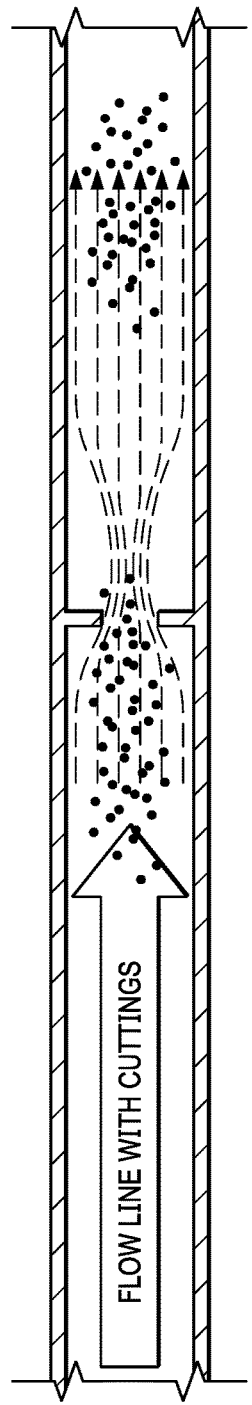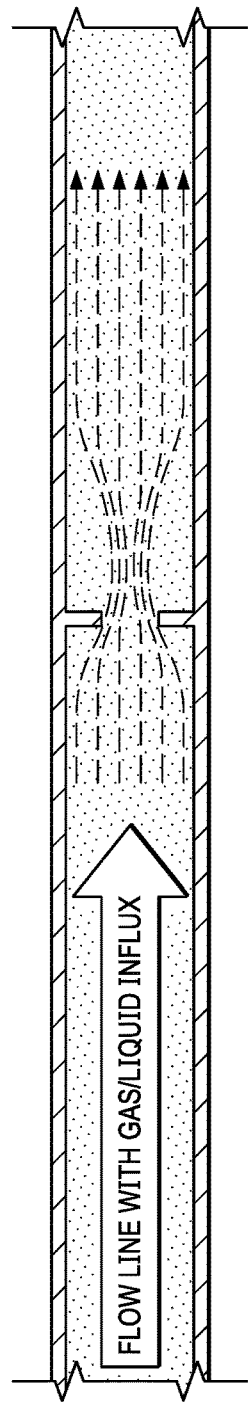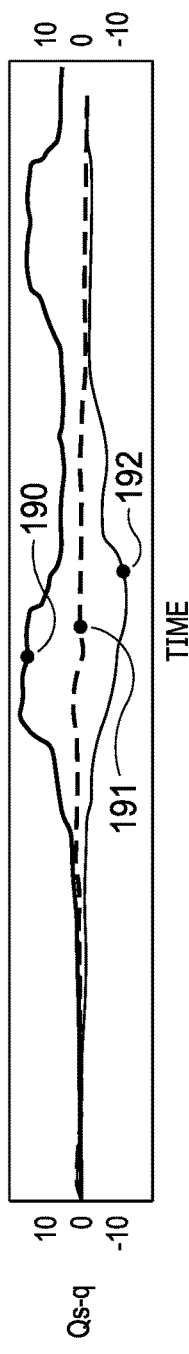

REAL TIME FLOW RATE METER

TECHNICAL FIELD

This disclosure relates, in general, to a real time flow rate meter and, more particularly, to a real time calibrated flow rate meter equipment using an orifice plate or venturi meter that enables calibration of cuttings transport models used in drilling programs, among other features.

BACKGROUND

Without limiting the scope of the present disclosure, its background will be described with reference to an environment used for producing fluid from a hydrocarbon bearing subterranean formation, as an example. Natural resources, such as oil or gas, residing in a subterranean formation can be recovered by drilling a wellbore that penetrates the formation. A variety of fluids can be used in both drilling and completing the wellbore and in resource recovery. Example fluids include drilling fluids, also called mud that may be pumped into the wellbore during drilling and similar operations; spacer, which helps flush residual drilling fluid from the well bore; and fracturing fluids, which may be used to enhanced oil or natural gas recovery.

During the completion of a well that traverses a hydrocarbon bearing subterranean formation, or during downhole cleaning operations, changes in content of fluid flow can have impacts on efficiencies or safety of the operations. Event detection of fluid density or viscosity changes are useful to alert operators for monitoring or for altering operational parameters, such as, e.g., drilling speed, for improved safety or increased production.

Accordingly, a need has arisen for improved real time detection of wellbore influx drilling fluid density or viscosity changes during well operations such as for forecasting mass flow rate of the influx.

BRIEF DESCRIPTION OF THE DRAWINGS

For a more complete understanding of the features and advantage of the present disclosure, reference is now made to the detailed description along with the accompanying figures in which corresponding numerals in the different figures refer to corresponding parts and in which:

FIGS. 4A-4D illustrate different example scenarios using flow rate measurement of a flow rate meter of FIG. 3 as an event detection technique, according to principles of the present disclosure;

DETAILED DESCRIPTION

In the following detailed description of the illustrative embodiments, reference is made to the accompanying drawings that form a part hereof. These embodiments are described in sufficient detail to enable those skilled in the art to practice the disclosed subject matter, and it is understood that other embodiments may be utilized and that logical structural, mechanical, electrical, and chemical changes may be made without departing from the spirit or scope of the disclosure. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments is defined only by the appended claims.

As used herein, the singular forms "a", "an," and "the" are intended to include the plural forms as well, unless the context clearly indicates otherwise. It will be further understood that the terms "comprise" and/or "comprising," when used in this specification and/or the claims, specify the presence of stated features, steps, operations, elements, and/or components, but do not preclude the presence or addition of one or more other features, steps, operations, elements, components, and/or groups thereof. In addition, the steps and components described in the above embodiments and figures are merely illustrative and do not imply that any particular step or component is a requirement of a claimed embodiment.

Unless otherwise specified, any use of any form of the terms "connect," "engage," "couple," "attach," or any other term describing an interaction between elements is not meant to limit the interaction to direct interaction between the elements and may also include indirect interaction between the elements described. In the following discussion and in the claims, the terms "including" and "comprising" are used in an open-ended fashion, and thus should be interpreted to mean "including, but not limited to." "Downhole" refers to a direction towards the end or bottom of a well. "Uphole" refers to a direction generally towards the top of a well or towards the surface. "Downstream" generally refers to a direction generally towards a wellhead, or towards the end or bottom of a well. The terms "about" or "substantially" refers to within +/− 10%, unless context indicates otherwise.

Figure 1:
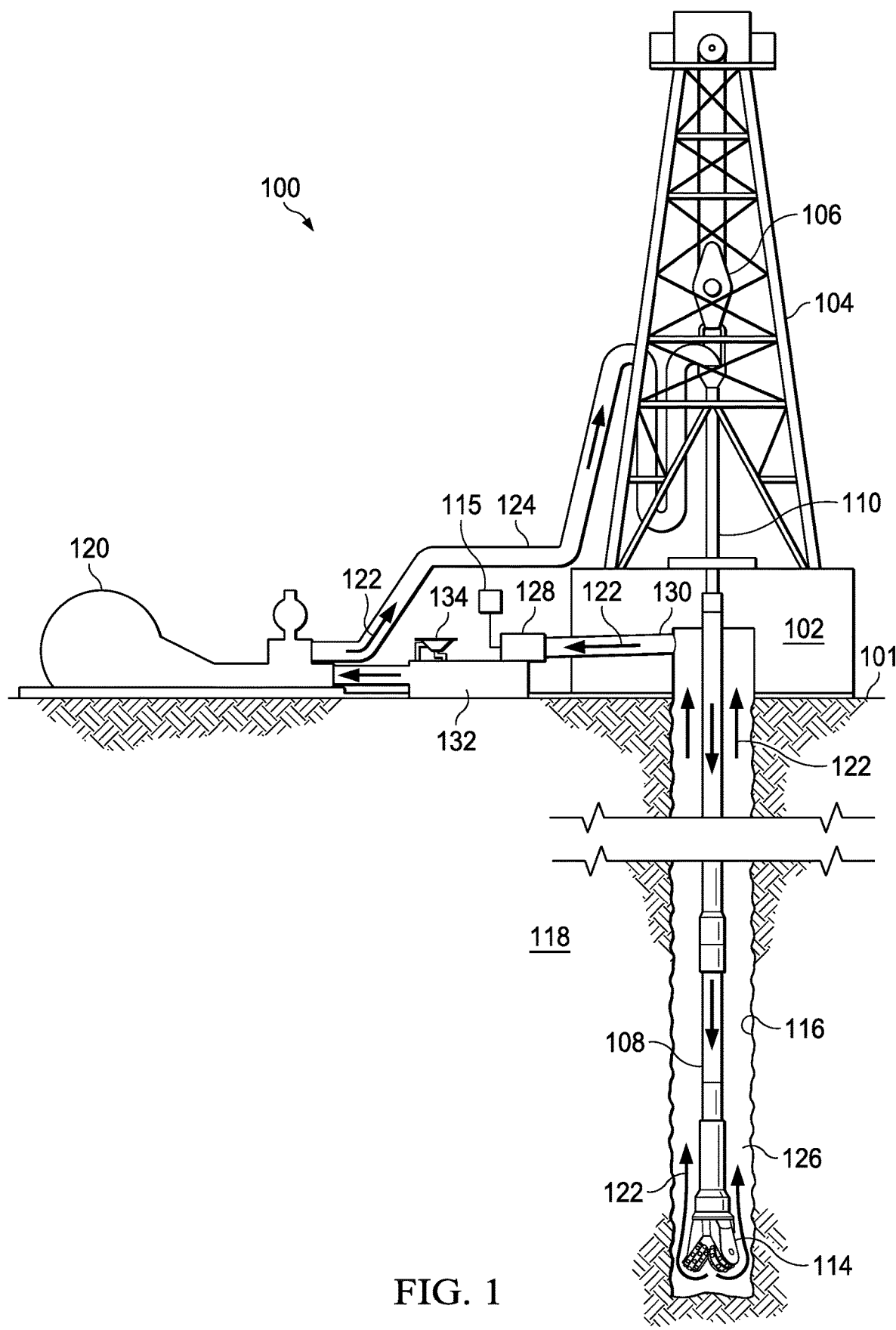
FIG. 1 is an illustration of an example wellbore drilling system employing a real time flow rate meter, according to principles of the present disclosure.

FIG. 1 is an illustration of an example wellbore drilling system 100 employing a flow rate meter, according to principles of the present disclosure. FIG. 1 is just one example of a drilling system configuration, and other configurations may be possible, as one skilled in the art would recognize. The drilling system 100 may include a drilling platform 102 that supports a derrick 104 having a traveling block 106 for raising and lowering a drill string 108. The drill string 108 may include drill pipe and coiled tubing, as generally known to those skilled in the art. A kelly 110 supports the drilling string 108 and is driven either by a downhole motor and/or via rotation of the drill string 108 from the well surface. As the drill bit 114 rotates, it creates a wellbore 116 that penetrates a subterranean formation 118. While wellbore 116 is shown as extending generally vertically into the subterranean formation 118, the principles herein are also applicable to wellbores that extend at an angle through the subterranean formation 118, such as horizontal or slanted wellbores.

A pump 120 (e.g., a mud pump) circulates drilling fluid 122 through a feed pipe 124 and to kelly 110, which conveys drilling fluid downstream through the interior of drill string 108 towards and through one or more orifices of the drill bit 114. The return drilling fluid 122 is then circulated uphole back to the surface 101 via an annulus 126 defined between the drill string 108 and the walls of the wellbore 116. At the surface 101, the recirculated or spent drilling fluid, i.e., return drilling fluid 122, possibly including hydrocarbons, exits annulus 126 and may be conveyed via interconnecting flow line 130 through a flow rate meter assembly 128, and onward to fluid processing units (not shown) and/or retention pit 132. A mixing hopper 134 may be present coupled to or in communication with the retention pit 132. The mixing hopper 134, which may be any of a wide variety of different mixing equipment, may be used to add materials to the drilling fluid 122.

The flow rate meter assembly 128 may comprise an orifice plate or a venturi configured within a return flow line, such as flow line 130, or another portion of the return fluid flow path. The orifice plate 145, or a venturi 129 (FIG. 5), creates a restriction in a flow conduit that causes a pressure drop across the plate or through the venturi. The flow rate meter assembly is described more fully below.

Figure 2:
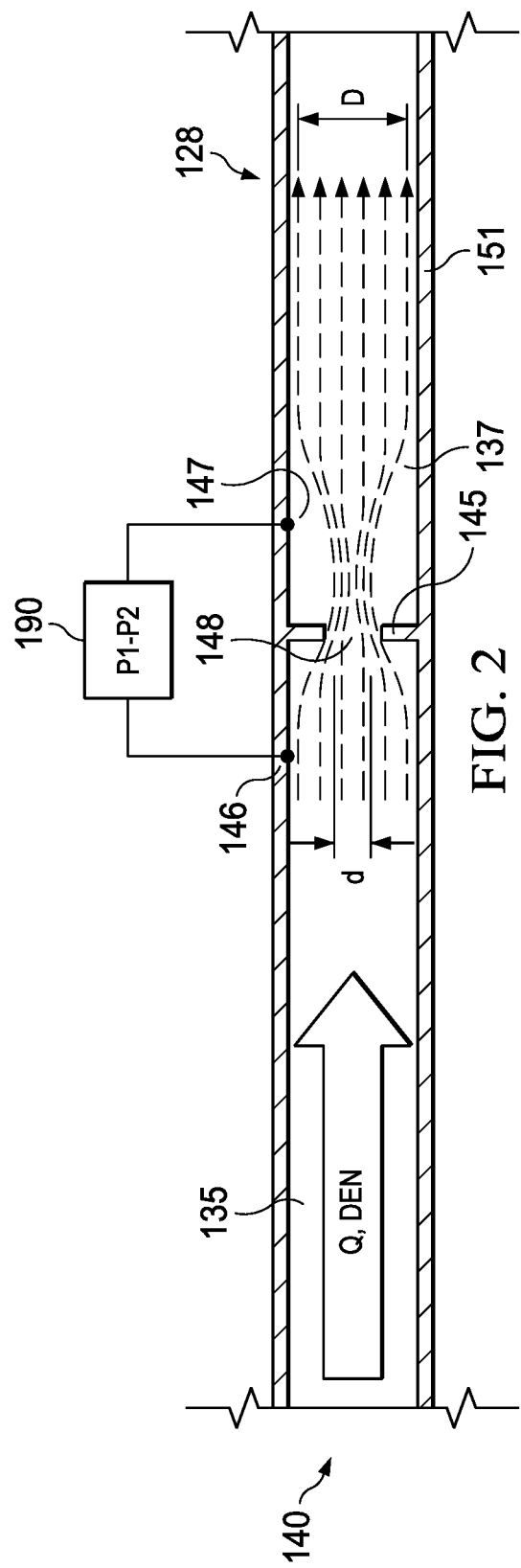
FIG. 2 is an illustration of a flow rate meter employing an orifice plate, according to an embodiment of the present disclosure.

FIG. 2 is an illustration of a real time flow rate meter assembly 128 employing an orifice plate 145, according to an embodiment of the present disclosure. The flow rate meter assembly 128 may be coupled to, attached to, or connected along a portion of a flow line, such as flow line 130 that conducts fluid 122 returning from a wellbore 116. The flow rate meter assembly 128 comprises a outer wall 151, which may be a circular pipe. Outer wall 151 may be the same outer wall of flow line 130. Returning fluid flow enters 140 a flow rate meter assembly 128 (or 129) and is constricted at a first portion 135 prior to entering an orifice 148 in orifice plate 145. The fluid 122 may then re-expand in a second portion 137 of the flow rate meter assembly 128. A first pressure sensor 146 measures fluid pressure $P_1$ at the first portion 135 prior to the orifice plate 145. A second pressure sensor 147 measures pressure $P_2$ at the second portion 137, after fluid passes through the orifice 148. The orifice 148 may comprise an opening having a diameter ratio selected from a range of about 0.1 to about 0.95, as compared to a diameter of a flow pipe providing fluid 122 to the orifice plate 145, such as, e.g., an internal diameter of circular flow line 130. In some embodiments, the ratio may be selected from a range of about 0.2 to about 0.7.

Generally, traditional orifice types of devices are usually suited for fluids that have a fairly constant density and consistent viscosity. Basic operating physics is derived from the Bernoulli and continuity equations with the discharge coefficient, Cd, being selected and/or calibrated experimentally.

$$q = Cd\, A_2 [2(P_1-P_2)/\mathrm{Den}(1-(A_2/A_1)^2)]^{1/2}$$

where, $A_2$=orifice area (m$^2$), $A_1$=pipe area (m$^2$), d=orifice diameter (m), D=pipe inside diameter (m), $P_1-P_2$=differential pressure (N/m$^2$), q=flow rate (m$^3$/s), Den=fluid mass density (kg/m$^3$). $A_1=\pi\,(D^2/4)$. $A_2=\pi\,(d^2/4)$. $\pi=3.14159$.

Since drilling fluids may have various densities and viscosities, measurements of flow rates using traditional orifice plate techniques can have large errors. Without an ability to calibrate the discharge coefficient with fluid changes, it typically is not suitable for measuring flow rates in well systems. However, with real time calibration of the discharge coefficient with density and rheology data, an orifice plate (or venturi) can be used in a much more analytical manner. Some of the techniques include:

Viscosity and density data from a BaraLogix® (trademark of Halliburton Corporation) system, or similar system that can autonomously provide fluid density and rheology to calibrate the discharge coefficient. In this manner, overall performance is better to detect changes in fluid properties, such as changes in concentration or density. This technique performs well as a mass flux device or flow rate device for drilling fluids. Moreover, corrections for temperature of the fluid flowing through the flow rate meter can be applied, along with updated discharge coefficients based on density and viscosity measurements.

Detection of slugs and cuttings that cause density variations, or concentration changes, due to cutting concentration in the flow stream is now possible.

Detection of wellbore fluid influx is now possible and the ability to forecast the mass flow rate of the influx is possible with calibration.

With a calibrated flow meter, detection of treatment pills or spacers clearing the wellbore to predict the density of the mixed interface fluids in real time is possible. Integrating the measured density with the predicted density provides a real time analysis of the wellbore cleaning efficiency. In some cases, this may lead to an extended clean-up procedure being initiated to ensure proper wellbore cleanup has been achieved.

Figure 3:
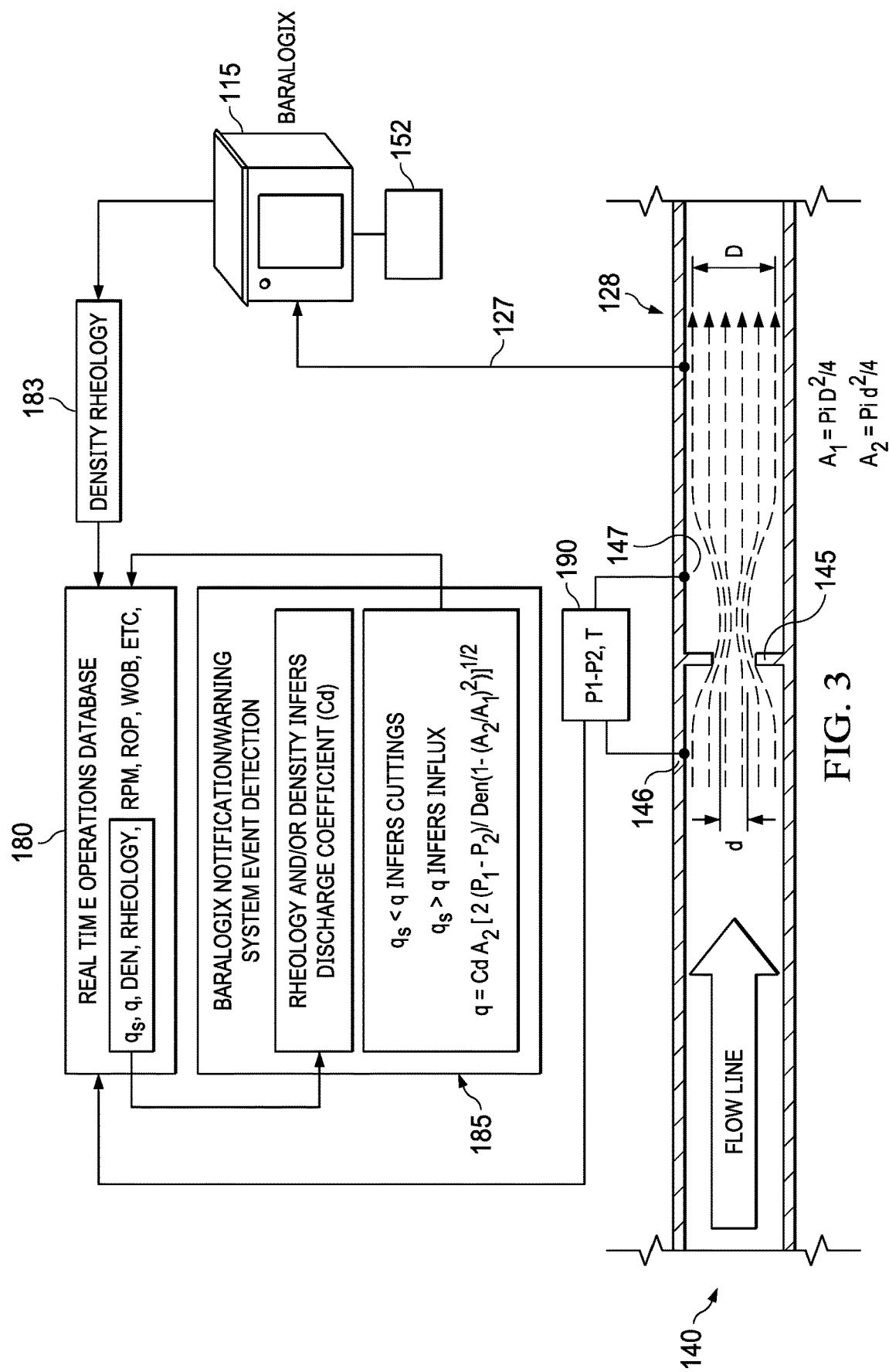
FIG. 3 is an illustration of the flow rate meter of FIG. 2, also showing flow of information, according to principles of the present disclosure.

FIG. 3 is an illustration of the flow rate meter of FIG. 2, also showing flow of information, according to principles of the present disclosure. The flow of information is shown occurring in relation to the flow rate meter assembly 128 (which may be flow rate meter assembly 129) and a BaraLogix® Density and Rheology Unit (DRU) 115 is a fully automated unit that can measure the density and rheology of drilling fluids and provides real time wellbore fluid rheology and density data. The BaraLogix® DRU 115 comprises a computer processing unit and memory for execution of the software to manage measuring and testing of the density and rheology of drilling fluids and for determining the fluid density and rheology 183 of the tested fluid. An input/output 152 device provides operator interaction. The BaraLogix® DRU 115 may be installed at the rig site, near the mud tanks, and may be skid mounted. The BaraLogix® DRU 115 may be equipped with one or more connections 127 to a mud supply line, e.g., feed pipe 124, and return lines, e.g., flow line 130, for ascertaining fluid density. In embodiments, large particles, such as cuttings, may be screened from the fluid before measurements are made for determining when and the approximate volume of cuttings passing through the flow line.

A real-time operations database 180, which may be a part of the BaraLogix system 115, or a remote database such as an InSite® database (InSite® is a registered trademark of Halliburton Corporation), may monitor rotations per minute (RPM) of the drill bit, rate of penetration (ROP), and weight on bit (WOB), given the fluid density and rheology 183 from the BaraLogix® DRU 115, and flow rate information from flow rate meter assembly 190. The flow rate meter assembly 190 may provide output data to the BaraLogix® DRU 115 and/or the real-time operations database 180, if the real-time operations database 180 is implemented separately from the BaraLogix® DRU 115. These are related to the drilling mechanics and ideally are monitored/controlled to obtain an optimal performance of a drilling operation.

An event notification system 185, which may be a part of the BaraLogix® DRU 115, may monitor for an event given the fluid density and rheology 183, q (flow rate at the flow meter), t (temperature, typically taken at the flow rate assembly 190), and $q_s$ (flow rate proximate or within a fluid pump, e.g., at pump 120 provided to BaraLogix® DRU 115). Rheology and/or density infers discharge coefficient Cd. Therefore, computing flow rate for both q and $q_s$ employing equation $q = C_d A_2 [2(P_1-P_2)/\text{Den}(1-(A_2/A_1)^2)]^{1/2}$ permits a determination as follows:

a) $q_s < q$ infers cuttings are present in the fluid flow, typically arising from the cutting due to the drill bit operations.

b) $q_s > q$ infers influx of hydrocarbons (and/or water).

Wellbore treatment fluids are subject to thermal expansion and hence a density change when they are heated. It is common for the flow line temperatures to exceed 120 F and in some extreme cases, the temperature might be as high as 200 F. This range of temperatures can cause a change in fluid density. For calibrating the Cd, the density of the fluid must be known at a reference temperature and then the density can be projected at any temperature for calibration purposes. The BaraLogix® unit provides this capability. The BaraLogix® unit measures density at the same temperature and is slightly pressurized to minimize gas bubbles. Thus, with a known starting temperature and the composition of the fluid, the fluid density at any temperature in the flow line can be predicted, thereby providing a calibrated system.

For a given orifice geometry, the discharge coefficient is a function of density ($\rho$), dynamic viscosity ($\mu$) and flow velocity (u), $Cd = f(\rho, \mu, u)$. A simple correlation can be expressed as $Cd = Cp \cdot Cc \cdot Cu$, where Cp is the velocity profile coefficient, Cc is the vena contracta coefficient (area ratio of the orifice) and Cu the viscosity coefficient. For low Reynolds number, Cp is invariant, Cc is unity and the instant above equation reduces to be proportional to $\sqrt{Re}$. This indicates that the viscous effect is dominant at the region. For turbulent flow at high Reynolds number, the typical orifice can be characterized by the Newtonian (e.g., water, base oil) in the turbulent region and the "clean" drilling fluid in the laminar region. This can be created offline to generate a database for the correlation between the discharge coefficient and the fluid properties (density and rheology). A model can be created to quantitatively obtain the concentration of cutting contamination as well as gas/water influx. For expediency, a table look-up can be employed.

Figure 5:
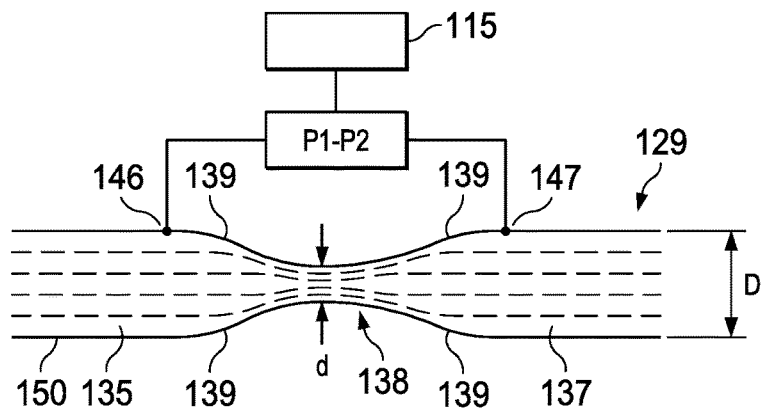
FIG. 5 is an illustration of a real time flow rate meter using a venturi meter, according to an embodiment of the present disclosure.

FIGS. 4A-4D illustrate different example scenarios using flow rate measurement of a flow rate meter of FIG. 3 or 5 as an event detection technique, according to principles of the present disclosure. The sensor 190 is not shown for simplicity, but is actually present. The pressure drop measurements shown in FIGS. 4A-4C demonstrate three possible cases for the response of a calibrated orifice plate 145 (or similarly, a venturi). FIG. 4A shows a normal calculated flow rate where $q_s$ and q are approximately equal, given a flow line with drilling fluid 140A. FIG. 4B shows a case where the measured pressure drop is higher because of cuttings increasing the effective density and viscosity of the fluids 140B passing through the flow meter. It is possible to note that cuttings can become slugs, due to a method of drilling operations normally used to enhance hole cleaning, i.e., periodic hole cleaning known as "pump and rotate." The viscosity and density of cuttings laden drilling fluid can be predicted based on the amount of hole drilled during a stand (ROP), and the pump rate and calibration tables used for the discharge coefficient. Additionally, the Thomas equation can be used to predict the increased viscosity of the fluid element due to the increased volume fraction of solids relative to the base fluid. Theory of the Thomas equation is explained in a technical article: Thomas, David G., 1965, Transport Characteristics of Suspension: VIII. A Note on the Viscosity of Newtonian Suspensions of Uniform Spherical Particles, *Journal of Colloid Science*, 20, pp. 267-277, which is incorporated by reference herein. Therefore, an average density and rheology because of the added cuttings can be computed that results in a Cd that accounts for a difference in a clean drilling fluid response relative to cuttings loaded fluid. Additionally, the cuttings transport model can be calibrated in real time. Similarly, an influx of formation fluids (e.g., hydrocarbons, water) lowers the fluid density and rheology causing $q_s$ to be greater than q. FIG. 4C shows a calculated flow rate where $q_s$ is greater than q indicating an influx with gas or liquid flowing 140C through the flow meter. FIG. 4D illustrates the results of FIGS. 4A-4C, where curve 190 represents cuttings detected, curve 191 represents and equal $q_s$ and q, while curve 192 represents an influx situation. These novel features permit event detection in real time, perhaps resulting in a change in operations, such as changing drilling speed, or taking action deemed appropriate due to the event.

FIG. 5 is an illustration of a real time flow rate meter using a venturi meter 129, according to an embodiment of the present disclosure. The principles of using a venturi is similar to the principle explained above in relation to the orifice plate 145, and may be substituted for the orifice type meter. The venturi meter 129 comprises a first portion 135 having a first pressure sensor 146 configured in or attached in the outer wall of a circular pipe, which may have a diameter similar or identical to a diameter of a flow line of the drilling system, and a portion of the outer wall 139 that narrows constricting incoming fluid flow 140 that passes through the narrowed portion 138. The fluid flow 140 passes through the narrowed portion 138 into a second portion 137 that has a second section 139, a wall that increases to the original size of flow line. The second portion has a second pressure sensor 147. The flow rate pressure sensor 190 is connected to the BaraLogix® DRU 115 and/or the real-time operations database 180.

Figure 6:
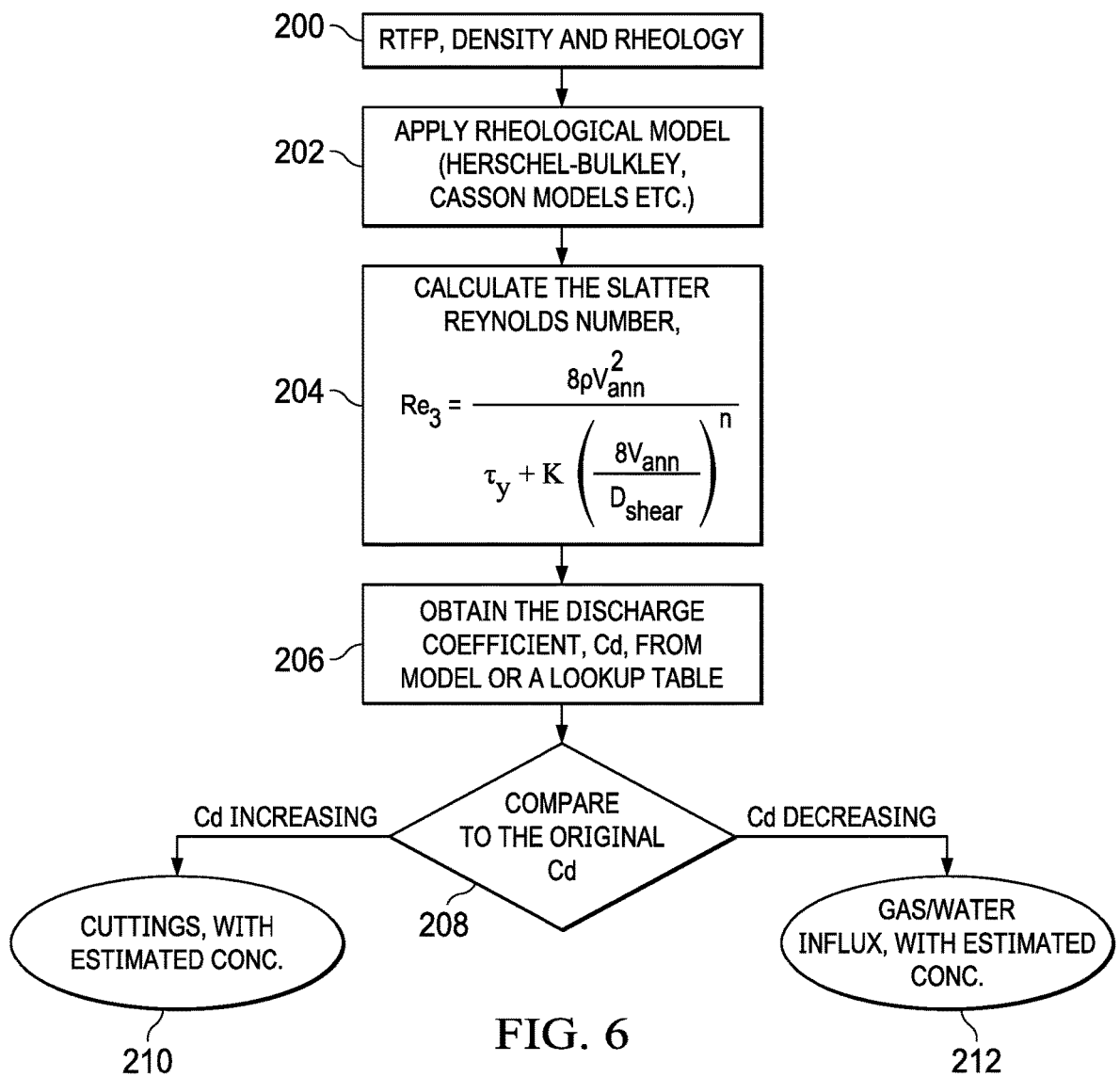
FIG. 6 is an example flow diagram showing steps of using a real time flow rate meter of FIGS. 2-5, the steps performed according to principles of the present disclosure.

FIG. 6 is an example flow diagram showing steps of using a real time flow rate meter of FIGS. 2-5, in a drilling situation, the steps performed according to principles of the present disclosure. At step 200, real time fluid properties, density and rheology are determined by a BaraLogix® DRU 115 of a drilling fluid being used in drilling operations. At step 202, a rheology model is applied. At step 204, the Slatter Reynolds number is calculated for non-Newtonian fluids (such as drilling muds) to yield stress behavior, where $\tau_y$ is the yield stress, K and n are rheology parameters from the Herschel-Bulkley model: $\tau = \tau_y + K\dot{\gamma}^n$ (with $\dot{\gamma}$ the shear rate), $\rho$ is the fluid density. $V_{ann}$ and $D_{shear}$ represents the mean velocity in the annulus and the shear portion diameter. At step 206, the discharge coefficient Cd is calculated or determined from a model or a look-up table. At step 208, the determined current discharge coefficient Cd is compared to an original Cd, or a previous Cd. If the current Cd is increasing compared with the original or previous Cd, then at step 210, the fluid is deemed to contain cuttings and an estimated concentration provided from the model or look up. If, however, the current Cd is decreasing compared with the original or previous Cd, then at step 212, the fluid is deemed to contain gas/water influx and an estimate of concentration provided from the model or look-up.

Based on the determination at step 208, action can be taken accordingly, For example, if cutting is deemed present at a specific concentration or higher, e.g., at step 210, action may be taken to slow down the drilling operation, such as reducing drill bit rotation rate. If influx is deemed present, e.g., step 212, at a specific concentration or higher, then predetermined safety measures may be taken, such as, e.g., to avoid a blowout.

In aspects of the disclosure, the following descriptions may apply.

Clause 1: A method for calibrating a discharge coefficient for well operations, comprising:
receiving a differential pressure indication of a rate of fluid flow in a flow line of a well operation;
determining viscosity and density data of the fluid flow;
determining a discharge coefficient using the differential pressure indication and the viscosity and density data;
comparing the determined discharge coefficient to a prior determined discharge coefficient of the fluid flow; and
ascertaining the presence of one of: cuttings in the fluid flow and influx in the fluid flow based on the comparing step.

Clause 2: The method of clause 1, wherein the differential pressure indication is received from an orifice plate flow rate sensing device.

Clause 3: The method of clause 1, wherein the differential pressure indication is received from a venturi flow rate sensing device.

Clause 4: The method of any one of clauses 1-3, wherein the step of determining a discharge coefficient using the differential pressure indication and the viscosity and density data includes using real time wellbore fluid rheology and density data.

Clause 5: The method of any one of clauses 1-4, wherein the discharge coefficient is calibrated with the viscosity and density data providing a calibrated flow rate sensing device.

Clause 6: The method of any one of clauses 1, 2, 4 or 5 wherein the step of receiving the differential pressure indication of a rate of fluid flow in the flow line is provided by a orifice plate flow meter.

Clause 7: The method of any one of clauses 1-6, further comprising comparing a flow rate at a flow meter measuring return fluid flow from a wellbore to a flow rate at a flow meter at a mud pump pumping fluid into a wellbore to detect a change in downhole conditions including at least one of: an influx of a fluid and a change in concentration of cuttings.

Clause 8: The method of clause 7, wherein the influx of a fluid includes at least one of a hydrocarbon and water.

Clause 9: The method of any one of clauses 1-8, wherein in the step of determining the discharge coefficient includes obtaining the discharge coefficient from a lookup table or from a model.

Clause 10: The method of any one of clauses 1-9, further comprising detecting slugs of cuttings in the fluid flow.

Clause 11: The method of any one of clauses 1-10, further comprising detecting treatment pills or spacers clearing a wellbore and predicting a density of mixed interface fluids in real time.

Clause 12: A method of calibrating a discharge coefficient for well operations, comprising:
calibrating in real time, a discharge coefficient using a pressure indication from an orifice flow meter assembly monitoring return drilling fluid flow from a wellbore, and using viscosity and density data of the return drilling fluid flow; and
detecting one of: cuttings and influx in the return drilling fluid flow.

Clause 13: The method of clause 12, further comprising detecting treatment pills or spacers clearing the wellbore.

Clause 14: The method of clause 12 or 13, further comprising predicting a concentration of the cuttings or predicting a mass flow rate of the influx.

Clause 15: The method of any one of clauses 12-14, further comprising comparing a flow rate of the return drilling fluid flow at the orifice flow meter with a flow rate at a pump pumping drilling fluid into the wellbore to detect a change in wellbore conditions.

Clause 16: A system for calibrating a discharge coefficient for well operations, comprising:
a flow rate meter that provides a pressure indication of return drilling fluid flow;
a device to determine a discharge coefficient using the pressure indication and viscosity and density data determined by density and rheology of the return drilling fluid flow; and
a device to identify cuttings or influx in the return drilling fluid flow based on the determined discharge coefficient and a prior determined discharge coefficient.

Clause 17: The system of clause 16, wherein the flow rate meter comprises a calibrated orifice plate flow rate meter.

Clause 18: The system of clause 16, wherein the flow rate meter comprises a venturi flow rate meter.

Clause 19: The system of any one of clauses 16-18, wherein the device to identify cuttings or influx further detects treatment pills or spacers clearing the wellbore.

Clause 20: The system of any one of clauses 16-19, wherein the device to identify cuttings or influx further detects slugs.

The embodiments set forth herein are merely illustrative and do not limit the scope of the disclosure. It will be appreciated that many other modifications and improvements to the disclosure herein may be made without departing from the scope of the disclosure.

We claim:

1. A method for calibrating a discharge coefficient for well operations, comprising:
receiving a differential pressure indication of a rate of fluid flow in a flow line of a well operation;
determining viscosity and density data of the fluid flow;
determining a discharge coefficient using the differential pressure indication and the viscosity and density data;
comparing the determined discharge coefficient to a prior determined discharge coefficient of the fluid flow; and
ascertaining the presence of one of: cuttings in the fluid flow and influx in the fluid flow based on the comparing step.

2. The method of claim 1, wherein the differential pressure indication is received from an orifice plate flow rate sensing device.

3. The method of claim 1, wherein the differential pressure indication is received from a venturi flow rate sensing device.

4. The method of claim 1, wherein the step of determining a discharge coefficient using the differential pressure indication and the viscosity and density data includes using real time wellbore fluid rheology and density data.

5. The method of claim 1, wherein the discharge coefficient is calibrated with the viscosity and density data providing a calibrated flow rate sensing device.

6. The method of claim 1, wherein the step of receiving the differential pressure indication of a rate of fluid flow in the flow line is provided by a orifice plate flow meter.

7. The method of claim 1, further comprising comparing a flow rate at a flow meter measuring return fluid flow from a wellbore to a flow rate at a flow meter at a mud pump pumping fluid into a wellbore to detect a change in downhole conditions including at least one of: an influx of a fluid and a change in concentration of cuttings.

8. The method of claim 7, wherein the influx of a fluid includes at least one of: a hydrocarbon and water.

9. The method of claim 1, wherein in the step of determining the discharge coefficient includes obtaining the discharge coefficient from a lookup table or from a model.

10. The method of claim 1, wherein in the step of ascertaining, the ascertaining detects slugs in the fluid flow.

11. The method of claim 1, further comprising detecting treatment pills or spacers clearing a wellbore and predicting a density of mixed interface fluids in real time.

12. A method of calibrating a discharge coefficient for well operations, comprising:
calibrating in real time, a discharge coefficient using a pressure indication from an orifice flow meter assembly monitoring return drilling fluid flow from a wellbore, and using viscosity and density data of the return drilling fluid flow;
comparing the determined discharge coefficient to a prior determined discharge coefficient of the return drilling fluid flow; and
detecting one of: cuttings and influx in the return drilling fluid flow based on the comparing step.

13. The method of claim 12, further comprising detecting treatment pills or spacers clearing the wellbore.

14. The method of claim 13, further comprising predicting a concentration of the cuttings or predicting a mass flow rate of the influx.

15. The method of claim 12, further comprising comparing a flow rate of the return drilling fluid flow at the orifice flow meter with a flow rate at a pump pumping drilling fluid into the wellbore to detect a change in wellbore conditions.

16. A system for calibrating a discharge coefficient for well operations, comprising:
a flow rate meter that provides a pressure indication of return drilling fluid flow;
a device to determine a discharge coefficient using the pressure indication and viscosity and density data determined by density and rheology of the return drilling fluid flow; and
a device to identify cuttings or influx in the return drilling fluid flow based on the determined discharge coefficient and a prior determined discharge coefficient.

17. The system of claim 16, wherein the flow rate meter comprises a calibrated orifice plate flow rate meter.

18. The system of claim 16, wherein the flow rate meter comprises a venturi flow rate meter.

19. The system of claim 16, wherein the device to identify cuttings or influx further detects treatment pills or spacers clearing the wellbore.

20. The system of claim 16, wherein the device to identify cuttings or influx further detects slugs.

* * * * *